United States Patent [19]

Hance

[11] 4,401,770

[45] Aug. 30, 1983

[54] SHOE INSOLE HAVING ANTIBACTERIAL AND ANTIFUNGAL PROPERTIES

[75] Inventor: James C. Hance, New Canaan, Conn.

[73] Assignee: Olin Corporation, New Haven, Conn.

[21] Appl. No.: 364,551

[22] Filed: Apr. 1, 1982

[51] Int. Cl.$^3$ ............................................. C08G 18/14
[52] U.S. Cl. .................................. 521/120; 521/157; 521/170; 523/122; 523/167
[58] Field of Search ...................... 521/120, 157, 170; 523/167, 122

[56] References Cited

U.S. PATENT DOCUMENTS

| | | | |
|---|---|---|---|
| 2,686,786 | 8/1954 | Shaw et al. | 523/122 |
| 2,742,393 | 4/1956 | Bernstein et al. | 523/122 |
| 2,809,971 | 10/1957 | Bernstein et al. | 523/122 |
| 3,536,260 | 10/1970 | Volz | 521/120 |
| 3,818,018 | 6/1974 | Weisse et al. | 260/294.8 J |
| 3,961,054 | 6/1976 | Furia et al. | 523/122 |

OTHER PUBLICATIONS

Cooney et al., *Polyurethane Foams and Foam Additives in Hydrocarbon Fuel-Water Systems,* Developments in Industrial Microbiology II, Chapter 21, pp. 210-224, (1970).

*Primary Examiner*—Lester L. Lee
*Attorney, Agent, or Firm*—William D. Sabo

[57] ABSTRACT

An improved shoe insole having antibacterial and antifungal properties comprising a flexible polyurethane foam which is prepared from a reaction mixture incorporating an effective antibacterial and antifungal proportion of a pyridinethione compound.

20 Claims, No Drawings

SHOE INSOLE HAVING ANTIBACTERIAL AND ANTIFUNGAL PROPERTIES

This invention relates to an improved shoe insole having antibacterial and antifungal properties. It also relates to an improved compression-densified polyurethane foam product adapted for use in making shoe insoles with antibacterial and antifungal properties.

Various pyridinethione compounds having antibacterial and antifungal properties are known in the art. See for example U.S. Pat. Nos. 2,686,786; 2,809,971; and 3,818,018. Some of these compounds have found widespread utility in antidandruff shampoo compositions and in skin cleansing compositions. Salts of 1-hydroxy-2-pyridinethione have also been employed in polyurethane foams which are used in fuel tanks, the compounds serving to inhibit the growth of certain microorganisms. See U.S. Pat. No. 3,536,260.

Various shoe insoles having antibacterial or antifungal properties are known in the art. For example, one product sold by COMBE Incorporated, White Plains, New York, under the trademark ODOR-EATERS ®, claims to employ an antibacterial fabric bonded to a latex foam containing particles of activated charcoal. Another insole sold by Scholl, Inc., Chicago, Ill., under the designation "Dr. Scholl's MULTI-LAYERED Odor Destroying Insoles", is a three layer construction. A top cloth layer is bonded to an activated charcoal layer, which in turn is bonded to a latex foam cushion. However, the art does not disclose an insole construction which includes a flexible polyurethane foam derived from a foam-forming reaction mixture containing an effective proportion of an antibacterial and antifungal agent.

Now, according to the invention, an improved shoe insole has been discovered. The shoe insole has antibacterial and antifungal properties and comprises: a flexible polyurethane foam prepared from a reaction mixture comprising: a polyol; an organic polyisocyanate; a foaming agent; a reaction catalyst; and an effective antibacterial and antifungal proportion of a pyridinethione compound. Further according to the invention, a compression-densified polyurethane foam having antibacterial and antifungal properties is prepared from the above reaction mixture. The use of this compression-densified foam is preferred in making the shoe insoles of the invention.

In accordance with the present invention, the improved shoe insole comprises a flexible polyurethane foam. In preparing the foam, either the so-called "one-shot method" or the "prepolymer technique" may be employed. Any combination of polyols, including polyether polyols and polyester polyols, organic polyisocyanate, foaming agent, catalyst and other reactants capable of forming a flexible polyurethane foam can be employed in carrying out the process of this invention, and the term "polyurethane foam-forming reaction mixture" in the specification and claims herein is intended to include any such combination. Typical formulations are described in U.S. Pat. No. 3,072,582, issued Jan. 8, 1963, and Canadian Pat. No. 705,938, issued Mar. 16, 1965.

While, as indicated above, both polyether and polyester polyols can be employed in the practice of this invention, preferred embodiments utilize polyether polyols in the preparation of the polyurethane foam-forming reaction mixture. Any suitable polyether polyol may be used for this purpose. These polyether polyols usually have a hydroxyl number less than about 250, and preferably in the range of about 25-175.

The polyether polyols include for example oxyalkylated polyhydric alcohols having a molecular weight range of about 700-10,000, and preferably about 1,000-6,000. These oxyalkylated polyhydric alcohols are generally prepared by reacting, in the presence of an alkaline catalyst, a polyhydric alcohol and an alkylene oxide such as ethylene oxide, propylene oxide, butylene oxide, amylene oxide, epichlorohydrin, and mixtures of these alkylene oxides, using either random or step-wise addition.

Any polyhydric alcohol which is suitable for preparing polyether polyols that are useful in making flexible polyurethane foam may be employed. Illustrative are ethylene glycol, propylene glycol, 2,3-butylene glycol, 1,3-butylene glycol, 1,5-pentane diol, 1,6-hexane diol, glycerol, trimethylolpropane, triethylolpropane, sorbitol, and the like, and mixtures thereof. If desired, a portion or all of the polyhydric alcohol may be replaced with another compound having at least two reactive hydrogen atoms, such as alkyl amines, alkylene polyamines, cyclic amines, amides, and polycarboxylic acids. It will be recognized that the reactive hydrogen compound can be one containing different functional groups having reactive hydrogen atoms. Mixtures of oxyalkylated polyhydric alcohols are also suitable for use in the process of this invention.

The organic polyisocyanates used in the preparation of the polyurethane foams include toluene diisocyanate, such as the 4:1 mixture or the 65:35 mixture of the 2,4- and 2,6-isomers, ethylene diisocyanate, propylene diisocyanate, methylene-bis-4-phenyl isocyanate, 3,3'-bitoluene-4,4'- diisocyanate, hexamethylene diisocyanate, naphthalene-1,5-diisocyanate, polyphenylene polymethylene isocyanate, and the like, and mixtures thereof. The preferred organic polyisocyanate is toluene diisocyanate. The amount of isocyanate employed in the process of this invention should be sufficient to provide at least about 0.7 NCO group per hydroxyl group present in the reaction system, which includes the polyol as well as any additive or foaming agent employed. An excess of isocyanate compound may be conveniently employed; however, this is generally undesirable due to the high cost of the isocyanate compounds. It is preferable, therefore, to employ sufficient isocyanate to provide no greater than about 1.25 NCO groups per hydroxyl group, and preferably between about 0.9 and about 1.15 NCO groups per hydroxyl group. The ratio of NCO to OH groups times 100 is referred to as the "index".

The polyurethane foams are prepared in the presence of a foaming agent, reaction catalyst, and preferably a small proportion of a conventional surfactant. The foaming agent employed may be any of those known to be useful for this purpose. Illustrative are water and organic foaming agents containing up to about seven carbon atoms such as the halogenated hydrocarbons, lower molecular weight alkanes, alkenes, ethers and mixtures thereof. Typical halogenated hydrocarbons include, but are not limited to: monofluorotrichloromethane, dichlorofluoromethane, difluorodichloromethane, 1,1,2-trichloro-1,2,2-trifluoroethane, dichlorotetrafluoroethane, ethyl chloride, methylene chloride, chloroform, and carbon tetrachloride. Other useful foaming agents include lower molecular weight alkanes, alkenes and ethers such as methane, ethane, ethylene, propane, propylene, pentane, hexane, heptane, ethyl ether, diisopropyl ether, and the like, and mixtures thereof. The amount of foaming agent employed may be varied within a wide range. Generally, however, the halogenated hydrocarbons are employed in an amount from about 1 to about 50 parts by weight per 100 parts by weight of the polyol, and generally water is employed in an amount from about 1.0 to about 6.0 parts by weight per 100 parts by weight of the polyol.

The polyurethane foams are prepared in the presence of a catalytic amount of a reaction catalyst. The catalyst employed may be any of the catalysts known to be useful for this purpose, such as tertiary amines and metallic salts particularly stannous salts, and mixtures thereof. Typical tertiary amines include, but are not limited to, the following: N-ethyl morpholine, N-hydroxyethyl morpholine, triethylene diamine, triethylamine, trimethylamine, trimethylaminoethyl ethanol amine, and the like, and mixtures thereof. Typical metallic salts include, for example, the salts of antimony, tin and iron, e.g., dibutyltin dilaurate, stannous octoate, and the like. Any catalytic proportion of catalyst or catalyst mixture may be employed such as between about 0.1 and about 3.0 parts, and preferably between about 0.2 and about 2.5 parts, per 100 parts by weight of total polyol.

It is preferred in the preparation of the polyurethane foams of the present invention to employ minor amounts of a conventional surfactant in order to further improve the cell structure of the polyurethane foam. Typical of such surfactants are the silicone oils and soaps, and the siloxane-oxyalkylene block copolymers. U.S. Pat. No. 2,834,748 and T. H. Ferrigno, *Rigid Plastic Foams* (New York: Reinhold Publishing Corp., 1963), pages 38–42, disclose various surfactants which are useful for this purpose. Generally up to about 2 parts by weight of the surfactant are employed per 100 parts by weight of total polyol.

Various additives can also be employed to provide different properties, e.g., fillers such as barytes, clay, calcium sulfate, or ammonium phosphate may be added to lower cost. Ingredients such as dyes may be added for color, and fibrous glass, asbestos, or synthetic fibers may be added for strength. In addition, plasticizers, deodorants and antioxidants may be added.

According to the invention, there is included in the foam-forming reaction mixture an effective antibacterial and antifungal proportion of a pyridinethione compound. In the practice of the invention, the pyridinethione compound is employed in a proportion which is effective in inhibiting the growth of bacteria and fungi that cause skin infections, including ringworm, and athlete's foot and which does not adversely affect the cell structure and physical properties of the foam. The pyridinethione compound which is utilized in the reaction mixture is selected from the group consisting of:

(a) 1-hydroxy-2(1H)-pyridinethione compounds having the formula

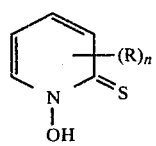

wherein R represents a member of the group consisting of hydrogen, lower alkyl, lower alkoxy and halo, and n is a positive integer less than 5; and the following salts thereof: alkali metal, alkaline earth metal, aluminum, heavy metal, amine-addition and quarternary ammonium;

(b) 2,2'-dithiobis-pyridine-1,1'-dioxide; and (c) adducts of 2,2'-dithiobis-pyridine-1,1'-dioxide, the adducts having the formula $(C_5H_4NOS)_2MY_t$ wherein M is an alkaline earth metal selected from the group consisting of calcium, magnesium, barium and strontium, Y is an anion selected from the group consisting of halides, sulfates, nitrates, chlorates and acetates, and t is either 1 or 2.

The 1-hydroxy-2(1H)-pyridinethione compounds listed in (a) above and their alkali metal and alkaline earth metal salts and the preparation of these compounds are described in U.S. Pat. No. 2,686,786 (issued Aug. 17, 1954 to Shaw, et al. U.S. Pat. No. 3,347,863 issued Oct. 17, 1967 to Ottmann, et al. discloses the aluminum salts of the above 1-hydroxy-2(1H)-pyridinethione compounds and their preparation. The heavy metal salts of the above 1-hydroxy-2(1H)-pyridinethione compounds and their preparation are described in U.S. Pat. No. 2,809,971 issued Oct. 15, 1957 to Bernstein, et al. The amine-addition salts and the quarternary ammonium salts of the above 1-hydroxy-2(1H)-pyridinethione compounds and their preparation are described in U.S. Pat. No. 2,742,393 issued Apr. 17, 1956 to Bernstein, et al. U.S. Pat. No. 2,742,476 issued Apr. 17, 1956 to Bernstein, et al. discloses 2,2'-dithiobis-pyridine-1,1'-dioxide and its preparation. The adducts of 2,2'-dithiobis-pyridine-1,1'-dioxide listed in (c) above and their preparation are described in U.S. Pat. No. 3,818,018 issued June 18, 1974 to Weisse, et al. The entire disclosures of all these patents are incorporated herein by reference.

A particularly preferred group of pyridinethione compounds for use according to the invention are: (a) 2-pyridinethiol-1-oxide, sodium salt (also known as 1-hydroxy-2(1H)-pyridinethione, sodium salt); (b) bis[1-hydroxy-2(1H)-pyridinethionato-O,S]-(T-4)-zinc; and (c) 2,2'-dithiobis-pyridine-1,1'-dioxide compound with magnesium sulfate (1:1). The most preferred compounds is bis[1-hydroxy-2(1H)-pyridinethionato-O,S]-(T-4)-zinc. These compounds are commercially available from Olin Corporation.

As noted above, the pyridinethione compound is used in an effective antibacterial and antifungal proportion. In practicing the invention any suitable proportion may be used provided it imparts to the foam the desired degree of antibacterial and antifungal proportion. Usually the pyridinethione compound is employed in a proportion ranging from about 0.01 to about 5.0 parts by weight based on 100 parts by weight of total polyol which is used in making the foam. In the more preferred embodiments of the invention from about 0.05 to about 0.5 parts of the pyridinethione compound are employed per every 100 parts of total polyol.

The selected proportion of the pyridinethione compound is incorporated in the foam-forming reaction mixture before foaming is commenced. Conveniently, the pyridinethione compound may be first blended with the polyol component or with one of the other reaction mixture components. The blend is then added to the other ingredients of the foam-forming reaction mixture.

It has been found to be preferable to employ a flexible polyurethane foam which is densified by compression. The compression-densified foams which are prepared have a density ranging from about 1.5 to about 15, and preferably from about 1.5 to about 10, pounds per cubic foot. Any convenient method may be utilized to permanently compress and thereby densify the foam. It is preferable to permanently reduce the foam to at least about ¾, and more preferably to between about ⅔ and about 1/10, of its original free-rise volume. Permanent foam compression may be achieved before or after the foam has become fully cured, using any convenient means such as crushing rolls or conveyors. Where the compression operation is carried out after the foam has become fully cured, additional means, such as heat, would ordinarily have to be used in order to permanently reset the foam in its compressed state. On the other hand, such additional means is usually not necessary when the foam is compressed before it has become substantially cured. The latter practice is preferred according to the method of the invention. This preferred practice is described in detail for example in U.S. Pat. No. 3,506,600 issued Apr. 14, 1970 to Zocco, et al., and in U.S. Pat. No. 4,252,517 issued Feb. 24, 1981 to Milford, et al. The entire disclosures of these two patents are incorporated herein by reference.

An illustrative batch process for permanently densifying the foam by compression comprises placing the foam-forming ingredients into a box or mold and allowing the ingredients to inter-react and fully expand into a foam. Before the foam becomes substantially cured, for example within 10 minutes after the expansion is completed, the foam is removed from the mold and compressed to a fraction of its original volume by means of compression rolls or conveyors. The compression is then removed and the foam allowed to become fully cured. Conveniently, the mold, into which the foam-forming reaction mixture is fed, may be of a selected dimension and configuration so that the final foam product can be used as is, or, if desired, after a trimming operation to remove the skin which usually forms on the foam surface.

An illustrative continuous process for permanently compressing the foam comprises admixing the foam-forming ingredients in a suitable mixing head and feeding the resulting mixture to a moving conveyor having suitable side retaining means to contain the liquid reactants. The side retaining means are necessary until the foam gels sufficiently to support its own weight. A crushing station, comprising for example a pair of crushing conveyors, is placed a certain distance downstream from the mixing head, so that the foam will be crushed at a specified crush time, the downstream distance being a function of the speed of the conveyor. A curing oven may be placed downstream from the crushing rolls to speed up the curing of the foam after it has been crushed; and, still farther downstream, a transverse cutter may be installed to cut the continuous flow of densified foam into sections of the desired length. If desired, means may also be provided downstream from the curing oven, for slicing or trimming off portions of the sides or the outer skin of foam, or for slicing the foam into longitudinal sections of the desired thickness.

The foam product obtained from the reaction mixture as described hereinabove is then employed in making shoe insoles. Because of the antibacterial and antifungal properties of the foam, it may be used as is (i.e., as a single layer without lamination to other materials) after suitable cutting operations to make a single layer insole product. It is also contemplated that the foam may be utilized in multi-layer constructions; and in certain applications, such multi-layer structures may be desirable. For example, a fabric layer may be bonded to the top surface of the foam for friction reduction and/or for aesthetic purposes. Other modifications within the scope of the invention will be apparent to those skilled in the art.

The shoe insoles of the present invention have many desirable features. In practicing the invention, there is obtained a foam product in which the pyridinethione compound is distributed in a substantially uniform manner. Also, it has been found that the pyridinethione compound will not readily leach out of the foam should the insole become wet. Other advantages will be apparent to those skilled in the art.

The following examples are provided to illustrate the invention. In these examples, all parts and percentages are by weight unless otherwise specified.

EXAMPLE 1

A polyurethane foam having a free-rise density of about 1.6 pounds per cubic foot was prepared from the following ingredients in the indicated proportions:

| Ingredients | Parts by Weight |
| --- | --- |
| Polyol ① | 100 |
| Water | 3.6 |
| Surfactant ② | 0.5 |
| Tertiary amine ③ | 0.18 |
| Stannous octoate ④ (50% solution in dioctyl phthalate) | 0.55 |
| Flame retardant additive ⑤ | 4.0 |
| Toluene diisocyanate ⑥, 110 Index | 47.8 |
| Pyridinethione compound ⑦ | 0.1 |

① A polyether triol having a molecular weight of 3,000, prepared by KOH catalyzed oxyalkylation of glycerin with propylene oxide.
② Commercially available silicone surfactant sold under the designation "Niax L-560" by Union Carbide Corporation.
③ Consisting primarily of tertiary amines and dipropylene glycol, commercially available under the designation "Dabco TL" from Air Products and Chemicals, Inc.
④ Commercially available under the designation "T-10" from M&T Chemicals, Inc.
⑤ Commercially available under the designation "THERMOLIN® 101" from Olin Corporation.
⑥ A mixture of toluene diisocyanate isomers (80:20 mixture of 2,4/2,6-isomers).
⑦ Bis [1-hydroxy-2(1H)—pyridinethionato-O,S]-(T-4)-zinc, commercially available under the designation "OMADINE" from Olin Corporation.

The above formulation was poured and allowed to foam in a box. When bubbles appeared on the surface of the foam, indicating completion of the expansion, the height of the foam bun was 5 inches. Within about 100 seconds from the time that the expansion was completed, the box was crushed in a hand press set at an opening of 2.5 inches. Throughout the foaming and crushing operations, the ambient temperature was about 75° F. After being compressed by the press, the foam was allowed to become fully cured. The resulting foam block was substantially open-cell. It had a final density of about 3.8 pounds per cubic foot and a final height of 2.7 inches.

EXAMPLE 2

The identical procedure of Example 1 was followed except that the reaction mixture contained 0.01 parts of the pyridinethione compound.

COMPARATIVE EXAMPLE A

For purposes of comparison, the identical procedure of Example 1 was followed except that the reaction mixture did not contain a pyridinethione compound.

TRIAL

The polyurethane foams of Examples 1 and 2 and Comparative Example A were then tested for activity against various microorganisms. The results of these tests are set forth in Table I.

In carrying out the tests, the following procedure was followed: Cores (18 mm) were randomly removed from each foam sample, and then cut into discs (8 mm). Triplicate sample discs were then dipped in aqueous suspensions containing each challenge organism at concentrations of 10⁷/ml (bacteria or yeast) or 10³/ml (mold). After incubation for the time period indicated in the Table, survivors were detected by picking up the discs with sterile forceps and then touching the discs on the surface of a Nutrient Agar (Difco) medium. All discs and detection media were incubated at 28° C. in darkness. The number in the table indicates the number of disc samples on which growth or survival of the challenge organism was detected.

TABLE I

Activity Against
Enterobacter aerogenes, Staphylococcus aureus, Candida albicans, and Trichophyton mentagrophytes

| Time (days) | Sample (Example No.) | Enterobacter aerogenes | Staphylococcus aureus | Candida albicans | Trichophyton mentagrophytes |
|---|---|---|---|---|---|
| 2 | A | 2 | 3 | 3 | 3 |
|   | 2 | 3 | 3 | 3 | 3 |
|   | 1 | 3 | 3 | 2 | 3 |
| 5 | A | 3 | 3 | 3 |   |
|   | 2 | 2 | 3 | 0 |   |
|   | 1 | 0 | 3 | 0 |   |
| 7 | A |   |   |   | 3 |
|   | 2 |   |   |   | 2 |
|   | 1 |   |   |   | 2 |
| 9 | A | 1 | 3 | 1 |   |
|   | 2 | 0 | 0 | 0 |   |
|   | 1 | 0 | 0 | 0 |   |
| 13 | A |   |   |   | 2 |
|   | 2 |   |   |   | 2 |
|   | 1 |   |   |   | 0 |

What is claimed is:

1. A shoe insole having antibacterial and antifungal properties comprising a flexible polyurethane foam prepared from a reaction mixture, comprising a polyol, an organic polyisocyanate, a foaming agent, a reaction catalyst and an effective antibacterial and antifungal proportion of a pyridinethione compound selected from the group consisting of:
   (a) 1-hydroxy-2(1H)-pyridinethione compounds having the formula

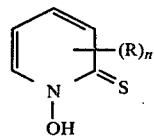

wherein R represents a member of the group consisting of hydrogen, lower alkyl, lower alkoxy and halo, and n is a positive integer less than 5; and the following salts thereof: alkali metal, alkaline earth metal, aluminum, heavy metal, amine-addition and quarternary ammonium;
   (b) 2,2'-dithiobis-pyridine-1,1'-dioxide; and
   (c) adducts of 2,2'-dithiobis-pyridine-1,1'-dioxide, said adducts having the formula $$(C_5H_4NOS)_2MY_t$$

wherein M is an alkaline earth metal selected from the group consisting of calcium, magnesium, barium and strontium, Y is an anion selected from the group consisting of halides, sulfates, nitrates, chlorates and acetates, and t is either 1 or 2.

2. The shoe insole of claim 1, wherein said polyol is a polyether polyol.

3. The shoe insole of claim 2, wherein said reaction mixture further comprises a surfactant.

4. The shoe insole of claim 3, wherein said compound is employed in a proportion ranging from about 0.05 to about 0.5 parts by weight based on 100 parts by weight of total polyol.

5. The shoe insole of claim 3, wherein said pyridinethione compound is selected from the group consisting of 2-pyridinethiol-1-oxide, sodium salt; bis[1-hydroxy-2(1H)-pyridinethionate-O,S]-(T-4)-zinc; and 2,2'-dithiobis-pyridine-1,1'-dioxide compound with magnesium sulfate (1:1).

6. The shoe insole of claim 5, wherein said pyridinethione compound is bis[1-hydroxy-2(1H)-pyridinethionato-O,S]-(T-4)-zinc.

7. The shoe insole of claim 5, wherein said polyether polyol is an oxypropylated polyhydric alcohol having a molecular weight of about 1,000–6,000 and said organic polyisocyanate is toluene diisocyanate.

8. The shoe insole of claim 7, wherein said polyether polyol is oxypropylated glycerin and said reaction mixture comprises water and a catalyst mixture of an amine and a stannous salt.

9. The shoe insole of claim 3, wherein said polyurethane foam is a compression-densified polyurethane foam having a density within the range from about 1.5 to about 15 pounds per cubic foot.

10. The shoe insole of claim 9, wherein:
said pyridinethione compound is selected from the group consisting of 2-pyridinethiol-1-oxide, sodium salt; bis[1-hydroxy-2(1H)-pyridinethionato-O,S]-(T-4)-zinc; and 2,2'-dithiobis-pyridine-1,1'-dioxide compound with magnesium sulfate (1:1);
said polyether polyol is an oxypropylated polyhydric alcohol having a molecular weight of about 1,000–6,000; and
said organic polyisocyanate is toluene diisocyanate.

11. The shoe insole of claim 10, wherein: said pyridinethione compound is bis[1-hydroxy-2(1H)-pyridinethionato-O,S]-(T-4)-zinc; said polyether polyol is oxypropylated glycerin; and said reaction mixture comprises water and a catalyst mixture of an amine and a stannous salt.

12. The shoe insole of claim 9, wherein said polyurethane foam is prepared by
   (a) placing a polyurethane foam-forming reaction mixture in a reaction zone and allowing the mixture to rise freely, thereby forming a partially cured cellular material, said reaction mixture being comprised of a polyol, an organic polyisocyanate, a foaming agent and a reaction catalyst;

(b) applying a compressive force to the partially cured cellular material after completion of the rise, thereby (c) reducing the volume of the partially cured cellular material to between about ¾ and about 1/10 of its original volume; and (d) removing the compressive force and completing the cure of the compressed cellular material.

13. The shoe insole of claim 12, wherein:

said pyridinethione compound is selected from the group consisting of 2-pyridinethiol-1-oxide, sodium salt; bis[1-hydroxy-2(1H)-pyridinethionato-O,S]-(T-4)-zinc; and 2,2'-dithiobis-pyridine-1,1'-dioxide compound with magnesium sulfate (1:1);

said polyether polyol is an oxypropylated polyhydric alcohol having a molecular weight of about 1,000–6,000; and said organic polyisocyanate is toluene diisocyanate.

14. The shoe insole of claim 13, wherein: said pyridinethione compound is bis[1-hydroxy-2(1H)-pyridinethionato-O,S]-(T-4)-zinc; said polyether polyol is oxypropylated glycerin; and said reaction mixture comprises water and a catalyst mixture of an amine and a stannous salt.

15. A polyurethane foam prepared from a reaction mixture comprising a polyol, an organic polyisocyanate, a foaming agent, a reaction catalyst and an effective antibacterial and antifungal proportion of a pyridinethione compound selected from the group consisting of:

(a) 1-hydroxy-2(1H)-pyridinethione compounds having the formula

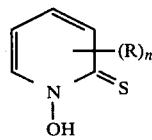

wherein R represents a member of the group consisting of hydrogen, lower alkyl, lower alkoxy and halo, and n is a positive integer less than 5; and the following salts thereof: alkali metal, alkaline earth metal, aluminum, heavy metal, amine-addition and quarternary ammonium;

(b) 2,2'-dithiobis-pyridine-1,1'-dioxide; and (c) adducts of 2,2'-dithiobis-pyridine-1,1'-dioxide, said adducts having the formula $(C_5H_4NOS)_2MY_t$ wherein M is an alkaline earth metal selected from the group consisting of calcium; magnesium, barium and strontium, Y is an anion selected from the group consisting of halides, sulfates, nitrates, chlorates and acetates, and t is either 1 or 2;

and wherein:

said polyurethane foam is compression-densified and has a density within the range from about 1.5 to about 15 pounds per cubic foot.

16. The polyurethane foam of claim 15, wherein said polyol is a polyether polyol and said reaction mixture further comprises a surfactant.

17. The polyurethane foam of claim 16, wherein said compound is employed in a proportion ranging from about 0.05 to about 0.5 parts by weight based on 100 parts by weight of total polyol.

18. The polyurethane foam of claim 16, wherein:

said pyridinethione compound is selected from the group consisting of 2-pyridinethiol-1-oxide, sodium salt; bis[1-hydroxy-2(1H)-pyridinethionato-O,S]-(T-4)-zinc; and 2,2'-dithiobis-pyridine-1,1'-dioxide compound with magnesium sulfate (1:1);

said polyether polyol is an oxypropylated polyhydric alcohol having a molecular weight of about 1,000–6,000; and said organic polyisocyanate is toluene diisocyanate.

19. The polyurethane foam of claim 18, wherein said pyridinethione compound is bis[1-hydroxy-2(1H)-pyridinethionato-O,S]-(T-4)-zinc; said polyether polyol is oxypropylated glycerin; and said reaction mixture comprises water and a catalyst mixture of an amine and a stannous salt.

20. The polyurethane foam of claim 16, wherein said foam is prepared by (a) placing a polyurethane foam-forming reaction mixture in a reaction zone and allowing the mixture to rise freely, thereby forming a partially cured cellular material, said reaction mixture being comprised of a polyol, an organic polyisocyanate, a foaming agent and a reaction catalyst;

(b) applying a compressive force to the partially cured cellular material after completion of the rise, thereby (c) reducing the volume of the partially cured cellular material to between about ¾ and about 1/10 of its original volume; and (d) removing the compressive force and completing the cure of the compressed cellular material.

* * * * *